United States Patent [19]
Arnold

[11] 4,214,871
[45] Jul. 29, 1980

[54] METHOD AND APPARATUS FOR CLEANING TEETH AND REMOVING PLAQUE

[76] Inventor: Carter H. Arnold, 317 Rocky Point Rd., Palos Verdes, Calif. 90274

[21] Appl. No.: 871,203

[22] Filed: Jan. 23, 1978

[51] Int. Cl.² .......................... A61C 3/02; A61K 5/00
[52] U.S. Cl. ...................................... 433/216; 433/88
[58] Field of Search .................. 32/58; 128/66, 62 A, 128/224, 229

[56] References Cited
U.S. PATENT DOCUMENTS

| | | | |
|---|---|---|---|
| 1,664,369 | 3/1928 | Maurer | 32/58 |
| 2,550,565 | 4/1951 | Hyser | 128/62 A |
| 2,672,143 | 3/1954 | Gold et al. | 128/66 |
| 2,814,877 | 12/1957 | Tilden | 32/58 |
| 3,214,775 | 11/1965 | Murov et al. | 128/229 |
| 3,568,667 | 3/1971 | Krieger et al. | 128/66 |
| 3,863,628 | 2/1975 | Vit | 128/66 |
| 3,971,136 | 7/1976 | Madsen | 32/58 |

*Primary Examiner*—Louis G. Mancene
*Assistant Examiner*—John J. Wilson
*Attorney, Agent, or Firm*—Albert M. Herzig; Edward C. Walsh

[57] ABSTRACT

A fast, efficient, economical method of daily oral hygiene designed for home use to replace the present ineffective methods such as brushing, water flushing, flossing, etc.

The method is particularly for removing plaque. A nontoxic and relatively nonabrasive solid material in pellet form is entrained in a stream of liquid, preferably water and discharged as a jet against the teeth and adjacent areas in the mouth. The pellets are of soluble material which preferably is halite and in various sizes generally in the range from 0.010 inches to 0.030 inches at the time of striking the teeth. The pellets strike with a point impact thereby having sufficient energy to remove plaque from the teeth. If any pellets should lodge under the gums they would dissolve thereby preventing a possible abscess. Mechanical apparatus of simplified form can be utilized to entrain the solid particles in the liquid stream.

12 Claims, 1 Drawing Figure

METHOD AND APPARATUS FOR CLEANING TEETH AND REMOVING PLAQUE

BACKGROUND OF THE INVENTION

1. Field of the Invention.

The field of the invention is that of treatment of the teeth and, more particularly, cleaning of the teeth by removing plaque therefrom.

2. Description of the Prior Art.

A basic problem is the removal of plaque from the crevices between teeth. Plaque is a formation of saliva mixed with food particles that adheres to the teeth and holds the bacteria that causes tooth decay, creates calculus and in time periodontal problems. It is extremely difficult and time consuming to remove plaque readily by way of brushing with a tooth brush or by way of dental floss or otherwise.

In the past many and various methods for plaque removal, such as brushing, vapor blasting, water blasting, solution application, etc. have been tried without success because each approach had one major deficiency or another.

As plaque is the primary cause of the tooth problems as described above, a complete solution to this problem has been sought for many years without success. Therefore, the conclusion is that the solution is not obvious.

Prior art patents include the following: U.S. Pat. Nos. 1,664,369; 2,550,565; 2,661,537; 2,759,266; 2,814,877; 2,828,135; 3,137,297; 3,192,922; 3,255,759; 3,344,524; 3,386,439; 3,971,136.

In the prior art, it has been known to discharge liquid cleaning material into the mouth and against the teeth using powders or minute abrasive particles entrained in the liquid.

It is not desirable to blow gas into the mouth because gas heats when compressed and freezes as it expands, thereby making a controlled temperature on the teeth extremely difficult, therefore causing extreme pain to the nerves of the teeth. Furthermore, the gas blows the particles around the mouth instead of flushing them out.

Abrasives, particularly under pressure, can cause objectionable wear to teeth and to the mechanical parts of the equipment used to deliver the material to the teeth.

All prior methods using sufficient pressure to obtain any cleaning effect whatsoever could drive particles up under the gums of the person which can then give rise to abscesses.

SUMMARY OF THE INVENTION

The method has been summarized briefly in the abstract.

In the method, pellets are used, and pellets of different sizes, because when they are injected into the mouth along with the water in pellet form, they have certain kinetic energy in accordance with the law of physics for kinetic energy $\frac{1}{2}mv^2$ and there is a point impact against the plaque on the tooth which is capable of removing the plaque.

The pellets are formed by crushing the halite to sieve size, that is, pellets are passed through a sieve which results in all different sizes between the diameters given above at the time of impact.

The optimum sizes at the present time are 10 to 30 thousandths in diameter, that is, that is the size at the time the pellet contacts the tooth. Small pellets are needed to get into the small areas and crevices between the teeth. The larger pellets due to greater mass will give a faster cleaning on the larger surfaces of the teeth. There is some dissolving action on the pellets after entrainment and prior to impingement, and accordingly, there is some reduction in size.

Soluble particles are used to accomplish the following:

Problems having arisen in the dental profession due to nonsoluble particles being driven under the gum line, thereby causing abscesses. However, soluble particles will dissolve, thereby eliminating this objectionable problem.

The particles used are nontoxic, so if injected or contacted by an open lesion, or injested, no harmful effects will result. If the particles are beneficial toward healing, such as sodium chloride particles, a double benefit results.

A minimum abrasive material is superior to the conventional abrasives as known in the prior art to minimize erosion of tooth enamel and dentin. Since all materials are more or less abrasive, the term "minimum abrasive" is used herein to mean less than 2.5 on the Mohs scale, approximately 35 Brinell or 44 Knoop under a 50 gram load.

With water it can be adjusted to a desirable temperature and when it goes into the mouth, it is effective to flush the particles out.

The outer surface of the teeth external to the gums is the enamel whereas the surface of the teeth under the gums is called cementum. When people get older, the gums tend to recede exposing the cementum which is a good deal softer than the enamel, so any harsh abrading method would be very bad for the cementum because it would rapidly abrade it away. Accordingly, in the method of the invention solid pellets are used which are softer than the enamel and dentin and approximately the same hardness of the cementum so that the plaque can be removed without abrading these surfaces of the teeth. If the cementum were abraded away, the dentin which is also softer than enamel but harder than cementum, would be attacked.

The minimum abrasive material does not primarily rely on the abrading action, but the kinetic energy released on impact to remove the plaque. This preserves the enamel of the tooth, and more importnat, the cementum under the gum line.

Particles instead of powder, slurry etc. are used for the following reasons:

With particles of a greater mass and of a greater density than one, and remaining intact until impact, the kinetic energy released is appreciably increased without the need for a highly abrasive material.

The combination of particles and water is more effective than water alone. When a globule of water impacts, the total force is expended over a large area. When a particle impacts, the total force is concentrated in a very small area, thereby increasing the P.S.I. exponentially.

Soluble particles are used to accomplish the following:

Problems having arisen in the dental profession due to nonsoluble particles being driven under the gum line, thereby causing abscesses. However, soluble particles will dissolve, thereby eliminating this objectionable problem.

It is an optimum consideration to have a very dense material so that small pellets will have substantial mass so that being injected at a certain velocity, they will have proportionate energy as necessary or appropriate to remove the plaque upon impact against it.

It is often suggested to patients with gum trouble that they should rinse out their mouths with sodium chloride dissolved in water. With respect to using pellets in the herein method, should they get up under the gum line, the action of saliva on them will be to dissolve the pellet and it will thereby be removed, plus the medicinal effect of rinsing out the mouth with the above solution.

The velocity of the water and the pellets is relatively high for effective practice of the method but, of course, not so high that velocity would be sufficient to do any damage to the teeth or the gums.

Using a liquid instead of a gas as a vehicle to carry soluble particles is advantageous in the invention. Gas heats when compressed and freezes as it expands, thereby making a controlled temperature on the teeth extremely difficult, therefore causing extreme pain to the nerves of the teeth. When using a liquid this is not a problem. Gas, under sufficient pressure, can eject particles of foreign matter from between closely adjacent members, but then has no residual flushing effect. When using a liquid the pressure does not have to be as great because of the higher density of liquids over gases, and liquids offer an exceptionally good flushing effect.

In the light of the foregoing, the objects of the invention may be summarized as follows:

The primary object is to realize a simplified but fully effective method of treating teeth to remove plaque on a daily basis.

A corollary objective is to realize a method as in the foregoing adapted for domestic use in the home by individuals.

A further object is to realize a method as in the foregoing that utilizes only simple, inexpensive materials and is adapted for use with a simplified device or instrumentality.

A further object is to realize a method as in the foregoing wherein soluble materials, preferably halite in pellet form, is entrained in a liquid, preferably water, and discharged against the teeth in such a way that the kinetic energy of the entrained pellets is capable of removing plaque from the teeth.

Further objects and additional advantages will become apparent from the following description and drawing.

DESCRIPTION OF THE SPECIFIC PREFERRED EMBODIMENT

Figure 1:
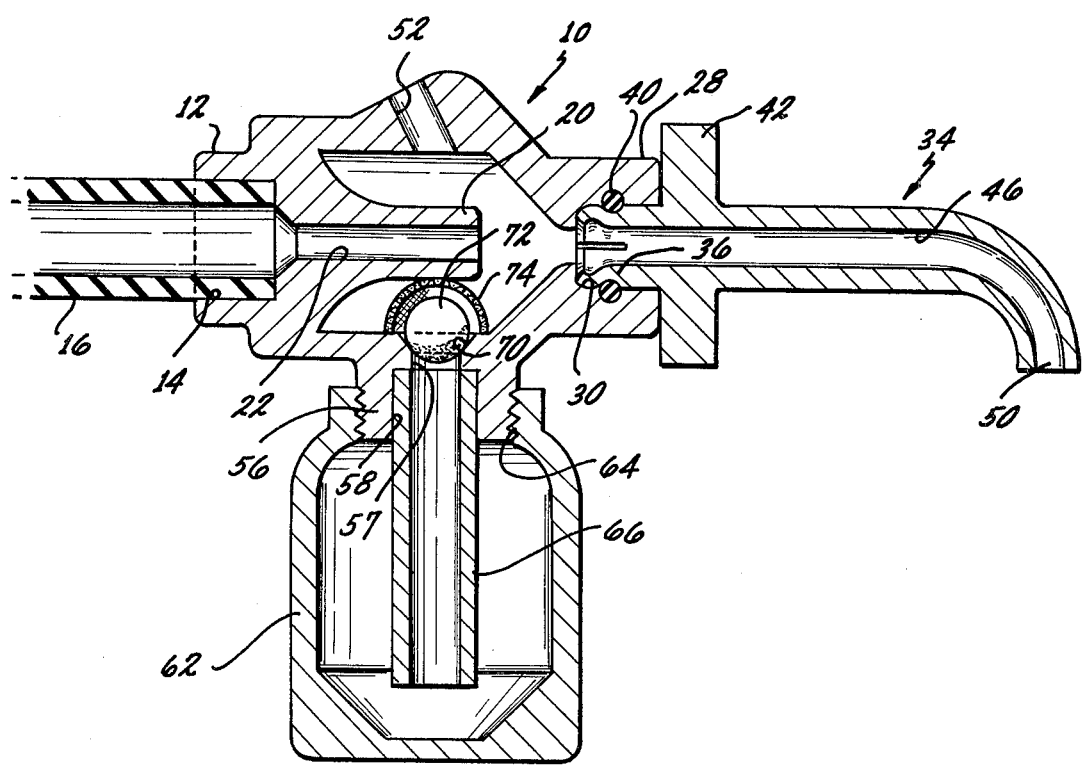
FIG. 1 is a schematic view of a simplified exemplary form of device or instrumentality practicing the invention.

The nature of the invention has been described in the foregoing. In a preferred embodiment of the invention, ordinary water is used in the method and the soluble material that is entrained in the water is halite in pellet form. The halite is readily available commercially and the pellets preferably are formed as previously described by crushing to sieve size, pellets passing through the sieve resulting in different sizes ranging in dimension from approximately 0.020 inches to 0.040 inches. The particles of pellet material, preferably halite, will typically conform to the following specifications and/or characteristics. The particles are in pellet form; are nontoxic; are soluble in the liquid used; have the characteristic of retarded disintegration, that is, solubility; have a higher density than water, a hardness not to exceed typically 44 Knoop under a 50 gram loan; are commercially available; and have optimum size as stated in the range of approximately 0.010 inches to 0.030 inches upon impact with the teeth.

The size of the particles or pellets at the outset, that is before entrainment, can readily be determined as described in the foregoing. The size of the pellets at the time of impact on the teeth will depend on various factors in actual utilization of the method. To some extent the size will depend upon the temperature and pressure of the water coming out of the tap and the actual density of the halite, the density of which can vary somewhat in its native condition. Another factor would be the actual distance of travel of the particles in the water stream after they have been entrained. Although these factors as explained will have a bearing on the size of the particles at impact, their effect is not such as to derogate from the practical effectiveness of the process utilizing the information set forth in the foregoing. Experimentation has demonstrated that the process is effective over a substantial range of sizes of particles before entrainment and a substantial range of sizes at the time of impact with the ranges as given herein maximum effectiveness of the process is realized in the minimum time. The technology herein represents the best mode of practicing the invention as presently known.

The single FIGURE of the drawing (FIG. 1) shows a simplified exemplary form of the device in which the invention can be practiced although it will be understood that the invention can be practiced in other types of uses which may be more elaborate. In the FIGURE, numeral 10 designates a body having a boss 12 at one end having a bore 14 in which is received the end of a tube 16 which can be any type of flexible tube through which ordinary water, such as tap water may be admitted to the device under pressure.

The body 10 has an internal venturi nozzle 20 that extends forwardly from the bore 14 to the venturi nozzle, having a bore 22 which is within the body 10 as shown. The body 10 has an outlet part 28 which has a bore 30 which receives a nozzle fitting 34. The nozzle has an inner end portion 36 that is received in the bore 30 and is sealed by an O-ring 40. The nozzle fitting 34 has a circular member or part 42 for rotating said nozzle which fits up against the end part 28 of the body 10. Nozzle fitting 34 has a bore 46 leading to its discharge end 50. The body 10 has an opening 52 in it as shown in a position so that this opening can be closed by the user's thumb when the device is held in the hand while treating the teeth. Removing the thumb breaks the vacuum and entrainment of particles is discontinued.

At the lower part of the body 10, there is an extending boss 56 which is externally threaded and which has a bore 57 and counterbore 58. Numeral 62 designates a container for the pellet material. The upper end of the container 62 has an opening which is internally threaded as designated at 64 and this end of the container is threaded onto the boss 56 as shown. Fitting in the counterbore 58 in the boss 56 is a tube 66 which extends down into the container 62 which holds the pellet material. The upper end of bore 57 has a chamber 70 forming a valve seat for a check valve which includes rubber ball check 72. Numeral 74 designates a wire retainer for ball 72.

UTILIZING THE METHOD

The method of the invention is practiced as follows.

The tube 16 in the FIGURE connects to any suitable water supply such as tap water. The pellets of halite are in the container 62. The supply volume and pressure of water may, of course, be controlled by a faucet or other valve. The water passing into and through the nozzle 20 has a venturi effect producing a lower pressure in the chamber within the body 10 before the water passes into the nozzle fitting 34. The user holds a thumb over the aperture 52 to preserve vacuum or venturi effect within the body 10. The lower pressure causes the solid particles within the container 62 to be picked up and entrained within the stream of water which is discharged through the nozzle fitting 34.

The user first directs the stream of water over and between the teeth to flush out foreign matter. After foreign matter has been flushed from mouth the thumb is applied to vacuum chamber orifice 52 thereby creating a vacuum which siphons halite pellets into the chamber, entraining the pellets with the water stream and projecting them against the tooth areas. As explained in the foregoing, the velocity of the stream of water with the entrained pellets is sufficient that the pellets have enough kinetic energy when they strike the teeth's surfaces or other areas with point impact to remove the plaque on the teeth. After performing their function in this manner, the particles and material will then be flushed out of the mouth with the water as it is removed therfrom.

From the foregoing, those skilled in the art will readily recognize the manner in which all the characteristics as described in the foregoing are present and how the objectives of the invention are realized.

The invention is able to achieve its basic purpose in the manner as explained in the foregoing, the invention not being subject to any of the drawbacks or deficiencies of the prior art. Although the invention is simple, it is extremely effective for its purpose.

The foregoing disclosure is representative of a preferred form of the invention and is to be interpreted in an illustrative rather than in a limiting sense, the invention to be accorded the full scope of the claims appended hereto.

What is claimed is:

1. A method of removing plaque from teeth including the steps of generating a controlled stream of liquid which can be discharged into the mouth, forming particles in pellet form and of a material which has a delayed solubility in said liquid and sufficient mass in pellet form so as to have kinetic energy when moving at the velocity of the stream of liquid, entraining the particles in the stream of liquid and jetting the stream with the entrained pellets into the mouth and against the teeth for removing plaque, whereby said delayed soluble pellets will dissolve if lodged under the gum line.

2. A method as in claim 1 wherein the particles are nontoxic and do not exceed a hardness at 44 Knoop under a 50 gram load.

3. A method as in claim 1 wherein the liquid is water and the particles are formed of halite.

4. A method as in claim 3 wherein the particles are at the time of impact on the teeth in sizes ranging from 0.010 inches to 0.030 inches.

5. A method as in claim 1 including the step of discharging the liquid with entrained particles against the teeth in a manner so that the particles have a point impact, the particles being of the size so that at the time of impact they have sufficient mass and velocity whereby the kinetic energy is sufficient to remove plaque from the teeth.

6. A method as in claim 5 including the step of forming particles having delayed solubility in the liquid.

7. A method as in claim 1 including the step of producing the said stream of liquid from liquid at ordinary line pressure.

8. A method as in claim 1 wherein the liquid is water and the particles have a density greater than one.

9. In a system for removing plaque from teeth, in combination, means for providing a stream of liquid and nozzle means whereby a jet of the liquid can be directed against teeth, a supply of pellets, and means for entraining the pellets in the liquid stream and for discharging them against the teeth with the liquid, the pellets being formed of a material which has sufficent mass when in pellet form to have enough kinetic energy when striking the teeth to remove plaque, the liquid being water and the pellets being particles formed from halide, the pellets being in sizes ranging from 0.010 inches to 0.030 inches.

10. In a system for removing plaque from teeth, in combination, means for providing a stream of liquid and nozzle means whereby a jet of the liquid can be directed against teeth, a supply of pellets, and means for entraining the pellets in the liquid stream and for discharging them against the teeth with the liquid, the pellets being formed of a material which has sufficient mass when in pellet form to have enough kinetic energy when striking the teeth to remove plaque, the material being soluble in the liquid so as to be dissolved in the event the pellets become lodged under the gum line.

11. A system as in claim 10 wherein the liquid is water and the pellets are particles formed from halite.

12. A system as in claim 11 wherein the pellets are provided in sizes ranging from 0.010 inches to 0.030 inches.

* * * * *